US010039496B2

(12) United States Patent
Yarger et al.

(10) Patent No.: US 10,039,496 B2
(45) Date of Patent: Aug. 7, 2018

(54) NEAR FIELD TELEMETRY LINK FOR PASSING A SHARED SECRET TO ESTABLISH A SECURE RADIO FREQUENCY COMMUNICATION LINK IN A PHYSIOLOGICAL CONDITION MONITORING SYSTEM

(71) Applicant: Becton, Dickinson and Company, Franklin Lakes, NJ (US)

(72) Inventors: Michael Yarger, Chapel Hill, NC (US); James Petisce, Westford, MA (US); Ellen DiResta, Arlington, MA (US); Deborah Burns, Westford, MA (US); David Mason, Newburyport, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 130 days.

(21) Appl. No.: 14/364,597

(22) PCT Filed: Dec. 14, 2012

(86) PCT No.: PCT/US2012/069860
§ 371 (c)(1),
(2) Date: Jun. 11, 2014

(87) PCT Pub. No.: WO2013/090791
PCT Pub. Date: Jun. 20, 2013

(65) Prior Publication Data
US 2014/0313052 A1    Oct. 23, 2014

Related U.S. Application Data

(60) Provisional application No. 61/576,309, filed on Dec. 15, 2011.

(51) Int. Cl.
*G08B 23/00* (2006.01)
*A61B 5/00* (2006.01)
(Continued)

(52) U.S. Cl.
CPC ............ *A61B 5/72* (2013.01); *A61B 5/14532* (2013.01); *A61B 5/7275* (2013.01); *A61B 5/742* (2013.01);
(Continued)

(58) Field of Classification Search
CPC ...................................................... A61B 5/002
(Continued)

(56) References Cited

U.S. PATENT DOCUMENTS 5,991,648 A    11/1999 Levin
2003/0036683 A1    2/2003 Kehr et al.
(Continued)

FOREIGN PATENT DOCUMENTS

JP    2002-073565    3/2002
JP    2007-529959 A    10/2007
(Continued)

OTHER PUBLICATIONS

Supplementary European Search Report dated Aug. 10, 2015 that issued in the corresponding Patent Application No. 12857131.2.
(Continued)

*Primary Examiner* — Amine Benlagsir
(74) *Attorney, Agent, or Firm* — Dickinson Wright PLLC

(57) ABSTRACT

A physiological condition monitoring system (e.g., a continuous glucose monitoring system) includes a physiological condition meter and a physiological condition sensor. The physiological condition meter and the physiological condition sensor are be placed in proximity to exchange a secret key using a near field wireless link, which is used to encrypt data to secure a radio frequency (RF) wireless channel.

31 Claims, 4 Drawing Sheets

(51) Int. Cl.
  *A61B 5/145* (2006.01)
  *G08C 17/02* (2006.01)
  *G16H 50/20* (2018.01)
  *G16H 15/00* (2018.01)
  *H04W 4/80* (2018.01)
  *A61B 5/024* (2006.01)
  *G06F 19/00* (2018.01)

(52) U.S. Cl.
  CPC ............ *G08C 17/02* (2013.01); *G16H 15/00* (2018.01); *G16H 50/20* (2018.01); *H04W 4/80* (2018.02); *A61B 5/002* (2013.01); *A61B 5/02438* (2013.01); *G06F 19/3456* (2013.01); *Y02A 90/26* (2018.01)

(58) Field of Classification Search
  USPC ........................................ 340/870.02, 870.01
  See application file for complete search history.

(56) References Cited

U.S. PATENT DOCUMENTS

| | | | |
|---|---|---|---|
| 2004/0266449 A1 | 12/2004 | Smetters et al. | |
| 2004/0266523 A1* | 12/2004 | Gentles | G07F 17/323 463/29 |
| 2005/0209515 A1 | 9/2005 | Hockersmith et al. | |
| 2007/0008140 A1 | 1/2007 | Saarisalo et al. | |
| 2007/0253021 A1 | 11/2007 | Mehta et al. | |
| 2008/0044014 A1 | 2/2008 | Corndorf | |
| 2008/0094226 A1* | 4/2008 | O'Shea | A61B 5/0002 340/573.1 |
| 2008/0175211 A1* | 7/2008 | Hansen | H04W 12/02 370/338 |
| 2008/0208627 A1* | 8/2008 | Skyggebjerg | A61M 5/14248 705/2 |
| 2009/0054737 A1 | 2/2009 | Magar et al. | |
| 2009/0115578 A1* | 5/2009 | Geissler | H04Q 9/00 340/10.1 |
| 2009/0140923 A1 | 6/2009 | Graves et al. | |
| 2009/0327724 A1 | 12/2009 | Shah et al. | |
| 2010/0045425 A1* | 2/2010 | Chivallier | A61B 5/0002 340/5.8 |
| 2011/0145894 A1* | 6/2011 | Garcia Morchon | G06F 19/3412 726/4 |
| 2011/0193704 A1 | 8/2011 | Harper et al. | |
| 2011/0237918 A1 | 9/2011 | Wagner et al. | |
| 2012/0299389 A1* | 11/2012 | Lee | H04B 5/0031 307/104 |

FOREIGN PATENT DOCUMENTS

| | | |
|---|---|---|
| JP | 2008-194323 | 8/2008 |
| JP | 2009-099083 | 5/2009 |
| WO | WO 2009/004578 A2 | 1/2009 |
| WO | WO 2009/119079 A1 | 10/2009 |
| WO | WO 2009/153710 A2 | 12/2009 |
| WO | WO 2010/007798 A1 | 1/2010 |

OTHER PUBLICATIONS

Japanese Official Notice of Rejection dated Nov. 22, 2016 which issued in the Japanese corresponding Patent Application No. 2014-547509, including Eng. translation.

* cited by examiner

NEAR FIELD TELEMETRY LINK FOR PASSING A SHARED SECRET TO ESTABLISH A SECURE RADIO FREQUENCY COMMUNICATION LINK IN A PHYSIOLOGICAL CONDITION MONITORING SYSTEM

FIELD OF THE INVENTION

The present invention disclosed and claimed herein generally relates to a physiological condition monitor (e.g., a continuous glucose monitor) and, more particularly, to methods and apparatuses to establish a near field telemetry link for passing a shared secret to establish a secure radio frequency communication link in a physiological condition monitoring system.

BACKGROUND OF THE INVENTION

Diabetes is a disease in which a person has high blood sugar either because the body does not produce enough insulin or because the person's cells are insensitive to the produced insulin. Accordingly, it is beneficial to monitor the person's glucose levels to identify trends in glucose levels, identify factors that affect glucose levels, evaluate foods and medications on glucose levels, and identify changes in a treatment plan.

A continuous glucose monitor (CGM) is an electronic system that measures and displays glucose level in a user's body. A CGM includes a sensor that is attached to a user's skin and held securely in place by a fastener. To measure glucose levels of the user, the sensor generally includes a metal filament that penetrates and rests in the fatty layer of the user's skin. The sensor communicates with a handheld meter that displays the glucose measurements from the sensor. A CGM is helpful to avoid potentially dangerous hyperglycemia or hypoglycemia and to help the user lower their average blood sugar levels over time.

Because the sensor is attached to the user's skin and the meter is a handheld device, wires would make the CGM difficult to use. Accordingly, CGM systems are preferably implemented with a wireless communication link between the sensor and the monitor. Accordingly, a separate transmitter may be incorporated into the sensor to transmit data to the handheld meter. Unique information must be exchanged between the transmitter and meter to create a secure communication link. Generally, for the user's convenience, the transmitter is implemented in a small form factor and includes a fixed battery that cannot be easily replaced. As such, the transmitter must be replaced when the battery is exhausted. Current CGM systems require the user to input information into the meter that identifies the transmitter, thereby allowing the meter to receive information from the sensor. This information is typically printed on the transmitter and, therefore, available for any person to read the information.

As such, the unique information can be easily obtained by observing unique information disposed on the transmitter or intercepting the communications with the unique information. Due to the importance of wireless medical devices, regulators have become interested in the security of such wireless medical devices. Further, because the user has to manually enter the unique information, replacing the transmitter is inconvenient. Moreover, battery life is an important factor in CGM sensors, and similar devices, where the battery is not designed to be replaced. Accordingly, there is a need for a method to exchange information for encrypting data in wireless medical devices that is convenient for users, and minimize battery usage.

SUMMARY OF THE INVENTION

A system and method for pairing a physiological condition meter and a physiological condition sensor in a wireless physiological condition monitoring system by exchanging a secret key is provided. The method comprises placing a physiological condition meter in proximity with a physiological condition sensor; receiving an instruction to initialize communication between the physiological condition meter and the physiological condition sensor; in response to the instruction, transmitting a secret key via a first wireless link; and transmitting measurement data to the physiological condition meter from a physiological condition sensor via a secure wireless link based on the secret key. In another illustrative method, the secret key is generated using a random process. In a further illustrative method, the data is encrypted using the secret key.

An illustrative wireless physiological condition monitoring system is disclosed. The wireless physiological condition monitoring system includes a physiological condition sensor for measuring physiological condition of a user and transmitting the measured physiological condition data using a secure link based on a secret key and a physiological condition meter for receiving the measured physiological condition data via the secure link based on the secret key and displaying the physiological condition data to the user. In the wireless physiological condition monitoring system, in response to an instruction, the secret key is generated and transmitted using a secure wireless link when the physiological condition sensor and the physiological condition meter are in proximity to each other.

Also disclosed is another illustrative method for synchronizing a wireless physiological condition monitor. The method comprises receiving an instruction to initialize communication between a physiological condition sensor and a physiological condition meter; in response to the instruction, transmitting a secret key via a wireless inductive link; receiving the secret key via the wireless inductive link; encrypting data to be transmitted between the physiological condition sensor and physiological condition meter; and transmitting the encrypted data between the physiological condition sensor and the physiological condition meter via a second wireless link. In other illustrative methods, the physiological condition meter and physiological condition sensor may be placed in electrical and/or optical contact, and the secret key may be transmitted via the electrical and/or optical contact.

DETAILED DESCRIPTION OF ILLUSTRATIVE EMBODIMENTS

Figure 1:
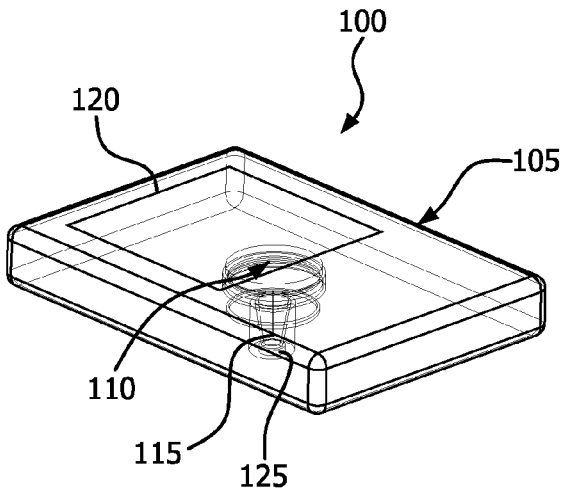
FIG. 1 depicts a CGM system in accordance with an illustrative embodiment of the present invention.

A near field telemetry link for passing a shared secret to establish a secure radio frequency communication link in a physiological condition monitoring system (e.g., continuous glucose monitoring system) is generally described herein. As will be described in detail below, an example glucose meter and an example glucose sensor of the CGM system are placed in proximity to exchange a secret key using a near field wireless link, which is used to pair the devices and encrypt data to secure a radio frequency (RF) wireless channel between the sensor and the monitor. As will be appreciated by one skilled in the art, there are numerous ways of carrying out the examples, improvements and arrangements of the methods disclosed herein. Although reference is made to the illustrative embodiments depicted in the drawings and the following descriptions, the embodiments disclosed herein are not meant to be exhaustive of the various alternative designs and embodiments that are encompassed by the disclosed invention.

Reference is now made in detail to the illustrative embodiments of the invention, which, together with the drawings and the following examples serve to explain the principles of the invention. These embodiments are described to enable those skilled in the art to practice the invention, and it is to be understood that other embodiments may be utilized without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the example methods, devices and materials are now described.

FIG. 1 depicts an illustrative embodiment of a CGM system 100. Generally, the CGM system 100 comprises a glucose meter 105 and a glucose sensor 110. In operation, the glucose meter 105 and the glucose sensor 110 communicate by a radio frequency (RF) wireless link. To establish the RF wireless link, the glucose meter 105 and the glucose sensor 110 must be linked together (paired) so that the glucose meter 105 only receives information from the paired glucose sensor 110 and not another nearby sensor or other unauthorized device. In the example of FIG. 1, the glucose sensor 110 and the glucose meter 105 securely exchange a secret key that is used to encrypt information transmitted on a different wireless link. That is, for example, the glucose sensor 110 uses the secret key to encrypt data that is transmitted to the glucose meter 105, which uses an identical secret key to decrypt the encrypted data. The glucose meter 105 may also preferably include an error check field in the decrypted data to verify successful reception and decryption of the received data.

The glucose sensor 110 typically includes a filament 115 that is inserted into the user's skin and rests in the fatty later beneath the user's skin. Other methods of sensor deployment (e.g., subcutaneous, intravenous, and so on) can be used as described below. In other examples, the glucose sensor 110 may be implemented by an optical sensor, a chemical sensor, or any device suitable for detecting a body characteristic or analyte such as glucose. As such, the user generally does not feel the filament 115 piercing the user's skin. To secure the position of the sensor, a suitable fastener such as an adhesive patch fixes the sensor in place. In the CGM system 100, the glucose meter 105 includes any suitable display 120 to provide graphical and/or textual information to the user, such as the user's current glucose level. However, the display 120 may provide the information in any suitable form, such as a line graph illustrating the glucose level over time. In such an example, the user is able to monitor their glucose level based on food and beverage consumption or other relevant events occurring throughout the day.

In the example of FIG. 1, the glucose meter 105 and the glucose sensor 110 preferably include a low power radio link by using inductive coupling of inductors in each device, which is also known as near field communication (NFC). When such inductors are placed in close proximity (e.g., 10 cm), the magnetic field generated by a current in a transmitting inductor will induce a voltage in a receiving inductor, thereby enabling a very short range wireless communication link. In the example of FIG. 1, after an instruction from a user or another indication that the glucose meter 105 and the glucose sensor 110 are close in proximity, the glucose meter 105 and/or glucose sensor 110 exchange a shared key using the NFC wireless link. As will be described below, the shared key is randomly generated data for encrypting communications between the glucose meter 105 and the glucose 110 using a different low power wireless link.

Because the glucose meter 105 and the glucose sensor 110 must be close in proximity due to the NFC wireless channel, security of the shared key is transmitted in confidence that another sensor is not nearby and can intercept the shared key. Further, the user is not required to enter information to manually pair the glucose meter 105 and the glucose sensor 110, thereby facilitating the operation of the CGM system 100 due to replacing a glucose sensor 110, for example. In another example, the glucose sensor must be placed in electrical and/or optical contact with the glucose meter and a secret key may be transmitted via the electrical and/or optical contact.

In the CGM system 100, the example glucose sensor 110 is a low power device that is typically replaced every 5-7 days. As such, the glucose sensor 110 is initially in a low power state or a powerless state to preserve its power source before being actuated to communicate with the glucose meter 105. Accordingly, to activate the CGM system 100, the glucose sensor 110 must be actuated (i.e., turned on) and the glucose meter 105 and the glucose sensor 110 must be exchange information to enable wireless communication to enable the CGM system 100.

To preserve power, the power source of the glucose sensor 110 may not be electrically coupled to the other electric devices in the glucose sensor 110 using, for example, any suitable latch or a switch. An operation by a user may cause the latch to close, thereby electrically coupling the power source to the electrical devices in the glucose sensor 110 to turn it on. For example, the glucose meter 105 in FIG. 1 includes a receptacle 125 configured to receive the glucose sensor 110. The receptacle 125 may also include a mechanical contact that biases a latch in the glucose sensor 110 to couple the power source to the electrical devices therein, thereby actuating the glucose sensor 110. The receptacle 125 may also include a switch (e.g., optical, mechanical, electrical, etc.) that detects the presence of the glucose sensor 110 when disposed therein.

In this example, when the glucose sensor 110 is disposed in the receptacle 125, the glucose sensor 110 is actuated and the glucose meter 105 is informed that the glucose sensor 110 is disposed in the receptacle 125 in a single step. In other examples, the user may initiate that the glucose sensor is proximate to the glucose meter by depressing a button disposed on the glucose meter 105 and/or the glucose sensor 110, for example. To enable communication, unique information must be exchanged to indicate that the transmitted data is provided from the glucose meter 105 and/or glucose sensor 110. As noted above, prior devices used a number unique on the device itself that identified it. However, the example glucose meter and/or the example sensor generate a secret key using a random process and exchange the secret key using the NFC wireless link. Using the secret key, the glucose meter 105 and glucose sensor 110 encrypt and decrypt data based on the secret key.

In a preferred embodiment, the glucose sensor 110 remains idle in a low or zero power state until the glucose meter 105 is brought into close proximity to the sensor. In this example, it will be understood that the roles of the sensor and meter may be exchanged, and only the example of the sensor remaining in a low power state until activated is provided herein. Both the sensor 110 and the meter 105 include an inductive element 208/308 for NFC communication. Preferably, the meter 105 is brought into close proximity to the sensor 110, and then the meter's inductive element 208 is energized. The energized inductive element 208 produces a magnetic field that induces a current in the sensor 105 inductive element 308 due to their close proximity. The sensor is preferably programmed to begin the pairing process when the appropriate current is induced in the inductive element 308 by the energized meter inductive element 208. Advantageously, this method avoids unnecessary battery drain that results from conventional methods of pairing including periodic polling. Moreover, the inductive nature of the pairing permits energy to be delivered to the sensor from the energized meter inductive element 308 due to the inductive link, further reducing battery drain, and even charging the battery of the sensor.

Further, the glucose meter 105 and the glucose sensor 110 may also exchange information relating to the health of the glucose sensor 110 (e.g., spoilage information, battery status, expiration date, etc.) to determine if the glucose sensor 110 is suitable for use. For instance, the glucose sensor 110 may transmit a preprogrammed expiration date to the glucose meter 105, which determines if the glucose sensor 110 is safe to use. In another example, the glucose sensor 110 may determine that it has spoiled by being exposed to a predetermined temperature for a particular period of time. As such, the glucose sensor 110 may transmit an indication of the duration it was exposed to the predetermined temperature to the glucose meter 105, which determines if the glucose sensor 110 is safe to use. In the event that the glucose meter 105 determines the glucose sensor 110 is not safe to use, the shared key is not exchanged to prevent use of the glucose sensor 110 with the glucose meter 105.

Figure 2:
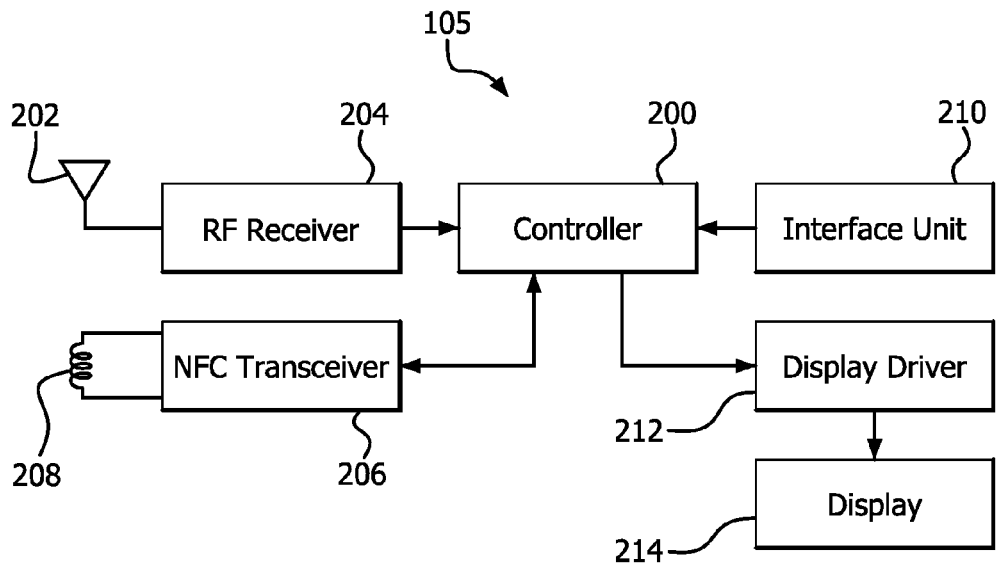
FIG. 2 depicts a block diagram of an example glucose meter for use in the CGM system of FIG. 1.

FIG. 2 illustrates a block diagram of an example glucose meter 105. Generally, the glucose meter 105 includes a controller 200 that is implemented by any suitable device to control the operation of the glucose meter 105 (e.g., a microcontroller, a microprocessor, an application specific integrated circuit, a functional programmable gate array, etc.). The controller 200 in the example of FIG. 2 includes an antenna 202 configured for receiving wireless communication signals and transmitting the received signals to an RF receiver 204, which converts (e.g., amplifies, demodulates, decodes, etc.) the received signal into data for the controller 200. In some examples, the controller 200 may need to process (e.g., decode, error check, etc.) the received data before use.

As described above, the glucose meter 105 also includes an NFC transceiver 206 for sending and receiving data over the NFC wireless link. In such an example, the NFC transceiver 206 receives data from the controller 200 to transmit the data via an inductor 208. As described above, a current flowing through the inductor 208 creates an electric field that induces a voltage in a corresponding inductor. Similarly, a voltage can be induced on the inductor 208 that is received by the NFC transceiver 206, thereby receiving a signal from a transmitting device. The NFC transceiver 206 receives the transmitted signal, converts it into the transmitted signal into data, which is then provided to the controller 200.

The controller 200 is coupled to receive data from an interface unit 210. The interface unit 210 is any suitable interface to operate the glucose meter. For example, the interface unit 210 may include a one or more buttons that allow the user to control the glucose meter 105. The controller 200 is further coupled to the display driver 212 to provide instructions thereto to control a display 214. That is, the controller 200 provides instructions to the display driver 212 to display information for the user's consumption. In some examples, the display driver 212 may be integral with the controller 200.

Figure 3:
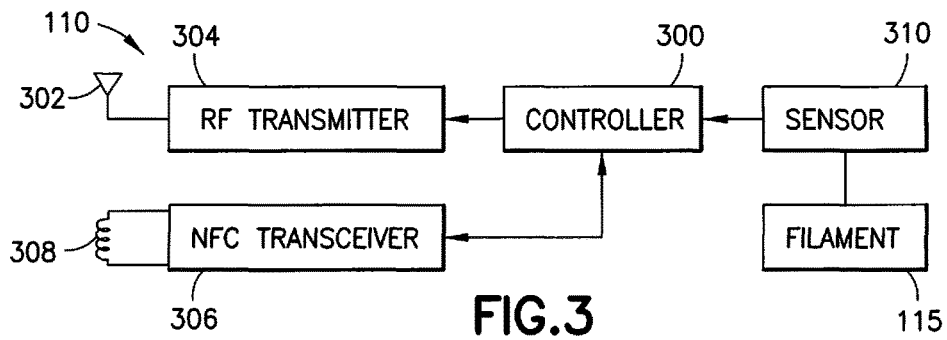
FIG. 3 depicts a block diagram of an example glucose sensor for use in the CGM system of FIG. 1.

FIG. 3 illustrates a block diagram of an example glucose sensor 110. Although the glucose sensor 110 is illustrated as a single device, it can be implemented by detachable modules that are fastened together. Generally, the glucose sensor 110 includes a controller 300 that is implemented by any suitable device to control the operation of the glucose sensor 110 (e.g., a microcontroller, a microprocessor, an application specific integrated circuit, a functional programmable gate array, etc.). The controller 300 is the example of FIG. 3 includes an antenna 302 configured for transmitting wireless communication signals and received signals from an RF transmitter 304, which converts (e.g., amplifies, demodulates, decodes, interleaves, etc.) data received from the controller 300 for transmission to a receiving device such as the glucose meter 105, for example. In some examples, the controller 300 may need to process (e.g., encode, generate error check data, etc.) the data before transmission.

As described above, the glucose sensor 110 also includes an NFC transceiver 306 for sending and receiving data over the NFC wireless link. In such an example, the NFC transceiver 306 receives data from the controller 300 to transmit the data via an inductor 308. In the event a current flows through the inductor 308, the inductor 308 creates an electric field that induces a voltage in a corresponding inductor. Similarly, a voltage can be induced on the inductor 308 that is received by the NFC transceiver 306, thereby receiving a signal from a transmitting device. The NFC transceiver 306 receives the transmitted signal, converts it into the transmitted signal into data, which is then provided to the controller 300. In other examples, the NFC transceiver 306 may be configured for simplex transmission as well.

The glucose sensor 110 also includes a sensor 310 that is configured to interface with the filament 115 and receive data therefrom. The sensor 310 converts the data into digital form and transmits the information to controller 300. Accordingly, the controller 300 receives the data and generates a glucose measurement of the user, and then transmits the measurement via the RF transmitter 304 to the glucose meter 105. Using the received data, the glucose meter 105 displays the current glucose measurement on its display 214. In another example, the sensor 310 may be integral with the controller 300. As noted above, the glucose sensor 110 may be modular such that different modules can be replaced at different time intervals. For example, the sensor 310 may be implemented in a separate module for replacement every week.

In the examples of FIGS. 2 and 3, the RF receiver 204 and the RF transmitter 304 are generally described using a simplex transmission scheme. However, in other examples, duplex communication may be required. As such, the glucose meter 105 and glucose sensor 110 would include an RF transceiver for duplex communication. Further, any suitable wireless link that allows encryption of traffic and an error check to determine that the data was properly decrypted may be implemented between the glucose meter 105 and glucose sensor 110. For example, a suitable communication link may be provided by standardized communication protocols such as ZigBee®, Bluetooth®, 802.11 related standards, radio frequency identification (RFID), and so forth. Generally, low power modes such as Bluetooth® low energy (BLE) are preferable due to the glucose sensor 110 being disposable.

Figure 4:
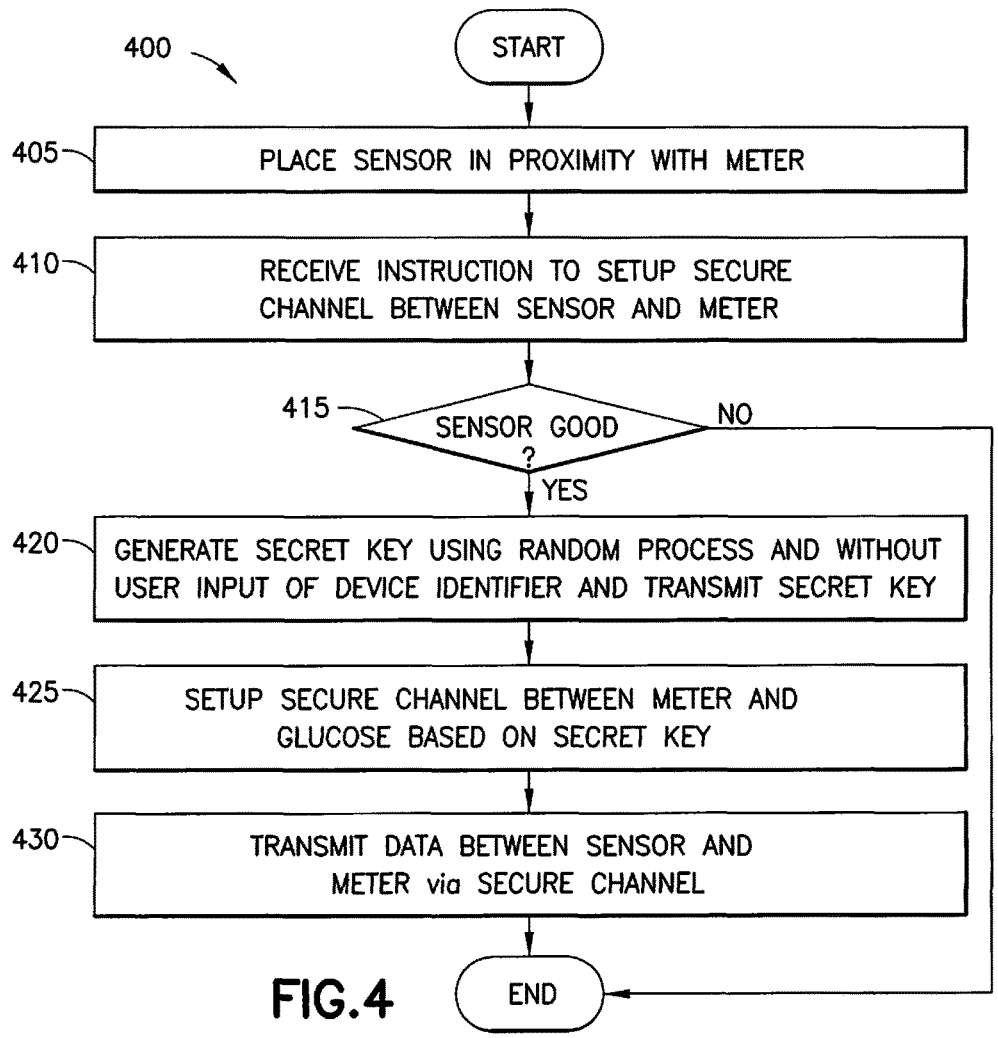
FIG. 4 is a flow chart of an illustrative process that the CGM system of FIG. 1 may implement to pair the glucose meter and the glucose sensor.

FIG. 4 illustrates an example process 400 of synchronizing the glucose meter and glucose sensor. The particular sequence of communications is described with reference to the data that is transmitted and received, but without reference to the transmitting or receiving device because the glucose meter and glucose sensor may perform either function. That is, the glucose meter could be the transmitter, receiver, or both. Similarly, the glucose sensor could be the transmitter, the receiver, or both.

Initially, the glucose sensor is placed in proximity with the glucose meter at block 405. Generally, the glucose sensor must be placed within range to initiate an NFC link, as described above. In some examples, the glucose sensor may be placed in a receptacle of the glucose meter. Preferably, the glucose meter inductor 208 is energized in close proximity to the glucose sensor inductor 308, such that a current is induced in the glucose sensor inductor 308. The induced current in the glucose sensor inductor 308 preferably triggers the pairing process to begin. At block 410, the example process 400 receives an instruction to setup a secure channel between the glucose sensor and the glucose meter. For example, in the event the glucose meter includes a receptacle having a detector to detect when the sensor is disposed therein, the glucose meter generates a signal to indicate to setup a secure channel with the glucose sensor. In other examples, the glucose meter and/or glucose sensor may include a switch that a user depresses to pair the glucose sensor with the glucose meter.

In response to the instruction provided at block 410, a determination is made if the glucose sensor is suitable for operation at block 415 using the NFC wireless link. For example, a determination is made that the glucose sensor has suitable battery power to operate for a required period (e.g., at least one day, etc.). In another example, a determination is made that the glucose sensor has not spoiled due to an expiration date or due to exposure to unsuitable environmental conditions (e.g., temperature, humidity, etc.). If the sensor fails the determination at block 415, the glucose meter cannot pair the glucose sensor and the example process 400 ends.

In the event that the sensor succeeds in the determination at block 415, the example process 400 generates a secret key and transmits the secret key over the NFC link so that both the glucose sensor and the glucose meter share the same secret key at step 420. In one example, the secret key is generated by any suitable random process for securing a wireless link. For example, the example process 400 may implement a cryptographically secure pseudorandom number generator to generate a 128-bit secret key. Because the glucose meter and the glucose sensor must be close in proximity, it is unlikely any other device will be nearby to receive or intercept the secret key. Further, once transmitted, there generally is no need to exchange the secret key again.

After both the glucose meter and the glucose sensor have identical secret keys, the glucose sensor and glucose meter setup a secure wireless channel that is different from the NFC link (e.g., Bluetooth® low power, ZigBee®, a custom wireless link, etc). In particular, the glucose meter and glucose sensor transmit data over the wireless channel that is encrypted using any suitable encryption algorithm (e.g., advanced encryption standard, data encryption standard, etc.) using the secret key, thereby forming a secure wireless link. In one example, using the data for transmission, the transmitting device generates an error check information such as a cyclic redundancy check (CRC) or a hash such as MD5, which is encrypted and transmitted with the data. The receiving device will decrypt the received information using the secret key and verify that the decryption is successful using the error check information. In another example, the CGM system 100 may verify that the secret key was successfully received before transmission of glucose measurement data over the secure wireless link.

After the glucose meter and the glucose sensor are transmitting the data via the secure wireless link at step 430, the example process 400 ends. Generally, the glucose meter or the glucose sensor will provide a perceptible indication to the user that communication has initiated and the user may fasten the glucose sensor to their skin.

Although example process 400 describes a particular sequence of events, the example process 400 and not limited and could be modified to perform all or some of the described functionality. For instance, determining that the sensor is suitable for operation at block 415 may be omitted.

FIGS. 5-8 illustrate examples of different sequences of communication between the glucose meter 105 and the glucose sensor 110 to implement the example process 400. In the described examples, the glucose meter 105 and glucose sensor 110 are close in proximity such that they communicate via the NFC wireless link. Unless otherwise indicated, the described communications are generally performed over the NFC wireless link until the secure wireless link is fully setup.

Figure 5:
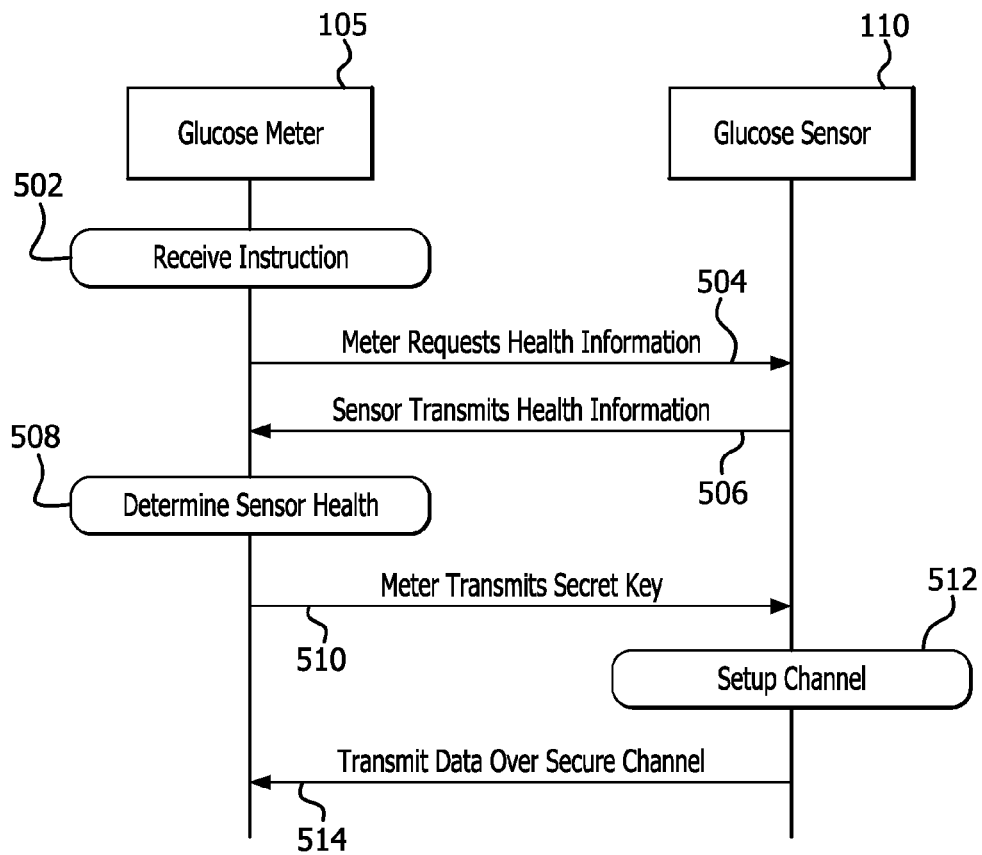
FIGS. 5-8 illustrate examples of communication sequences between the glucose meter and the glucose sensor according to the example process of FIG. 4.

FIG. 5 illustrates an example of a CGM system 100 that determines the health of the glucose sensor 110 before data transmission can begin. At step 502, the glucose meter 105 receives an instruction to setup a secure wireless link with the glucose sensor 110. In response, the glucose meter 105 transmits a request to the glucose sensor 110 for health information at step 504. In some examples, an initial message would indicate that the glucose meter 105 is requesting the information without explicit instructions. The glucose sensor 110 generates its health information (e.g., battery voltage, spoilage information, temperature information, expiration date, etc.) and transmits the health information to the glucose meter 105 at step 506. Using the received health information of the glucose sensor 110, the glucose meter 105 determines if the glucose sensor 110 is suitable for use in the CGM system at step 508. If the glucose sensor 110 is not suitable, the communications ends and the glucose sensor 110 is not paired with the glucose meter 105, as described above. For example, the glucose meter 105 could transmit a kill signal to the glucose sensor 110, which fully disables the glucose sensor 110.

If the glucose sensor 110 is determined to be suitable for use at step 508, the glucose meter 105 generates a secret key that is transmitted to the glucose sensor at step 510. As noted above, the secret key may be generated by any suitable random process for securing the wireless link. At step 512, the glucose sensor 110 stores the secret key and sets up the channel with the glucose meter 105. The glucose sensor 110 then begins transmitting data associated with a measurement of the user (e.g., glucose information, etc.) to the glucose meter at step 514 over the secure channel.

Figure 6:
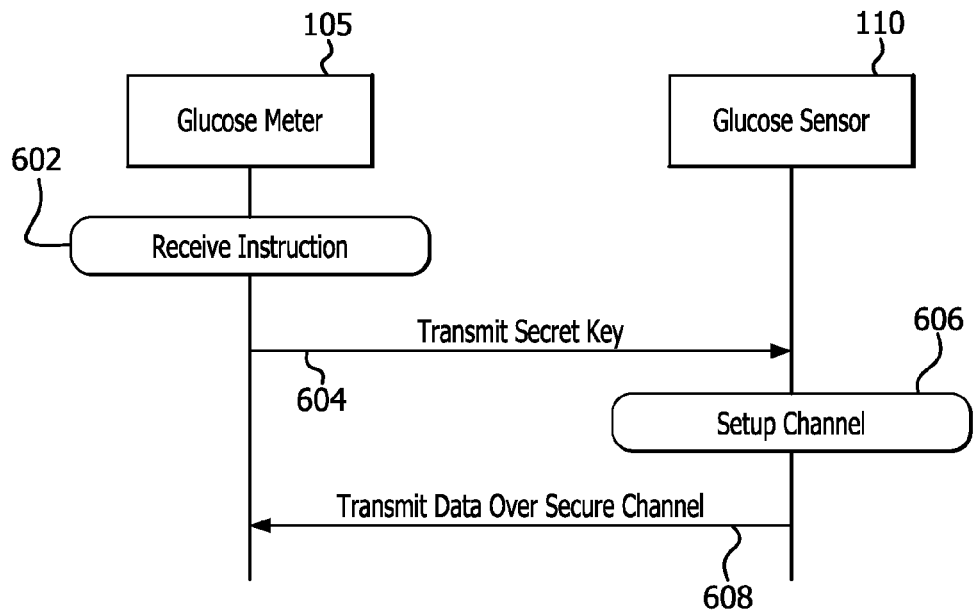

FIG. 6 illustrates another example of a CGM system that implements a passive glucose sensor that having a one-time programmable (OTP) radio frequency identification (RFID) tag. In such an example, at step 602, the glucose meter 105 receives an instruction to setup a secure wireless link with the glucose sensor 110. In response, the glucose meter 105 generates a secret key and transmits the secret key to the glucose sensor 110 at step 604. Using the received secret key, the glucose sensor 110 programs the secret key into its memory at step 606. For example, the glucose sensor 110 could include a Class 1 RFID tag that is programmable a single time with the secret key. In this example, the glucose meter 105 initiates reception of data using the secret key in response to transmitting the secret key. After the glucose sensor 110 has programmed the secret key, it begins transmitting data over the secure channel at step 608. In other examples, the glucose sensor 110 can be disabled by providing a kill instruction from the glucose meter 105.

In the example of FIG. 6, the OTP glucose sensor 110 implements a simple, low cost passive NFC link that provides limited functionality and is disposable. In this example, the glucose sensor 110 cannot be programmed with another secret key, thereby preventing it from being used again for safety purposes.

Figure 7:
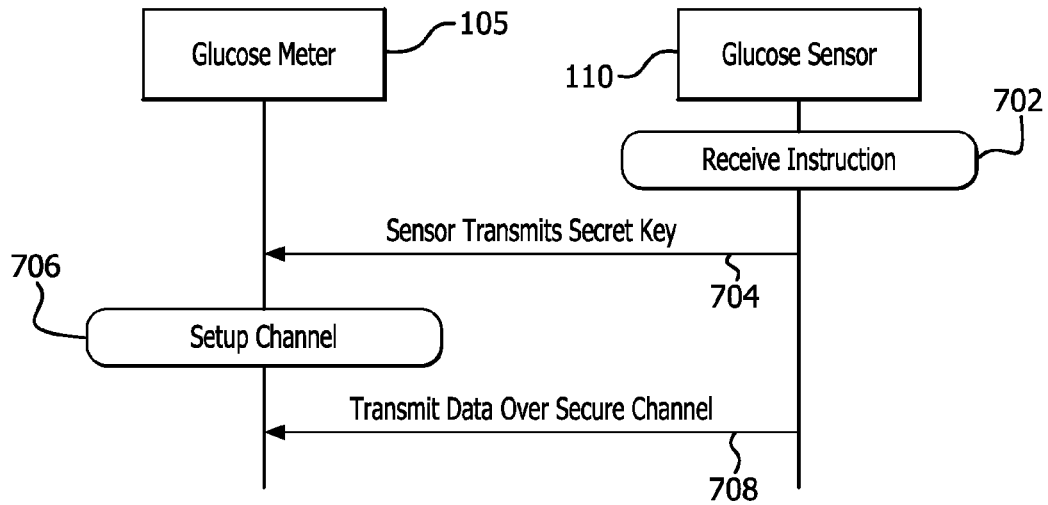

In other examples, the glucose sensor 110 may provide more functionality and thereby require a longer operational period. As such, it may be beneficial to enable the glucose sensor 110 to be reconfigured with the glucose meter 105. In the example of FIG. 7, at step 702, the glucose sensor 110 receives instruction to setup a secure wireless link with the glucose meter 105. In response, at step 704, the glucose sensor 110 generates a secret key and transmits it to the glucose meter 105. In response to receiving the secret key, the glucose meter 706 initiates reception of the wireless channel using the secret key at step 706. The glucose sensor 110 may wait a predetermined period of time (e.g., 1 second) for the glucose meter 105 to initiate data reception. After this period of time expires, the glucose sensor 110 transmits data over the secure channel at step 708.

In the example of FIG. 7, the glucose sensor 110 is reprogrammable and therefore can be reused. For instance, the glucose meter 105 may also include an insulin pump that is replaced monthly by the user. In such an example, the glucose meter 105 may need its power source (e.g. a battery, etc.) to be replaced, thereby requiring the secure wireless channel to be temporarily disabled. As such, after actuating the glucose meter 105 with a new power source, the glucose meter 105 and the glucose sensor 110 would exchange another secret key to initiate communication again. In another example, the battery in the glucose sensor 110 may be fastened such that it is not replaceable, and a new glucose sensor would be needed.

Figure 8:
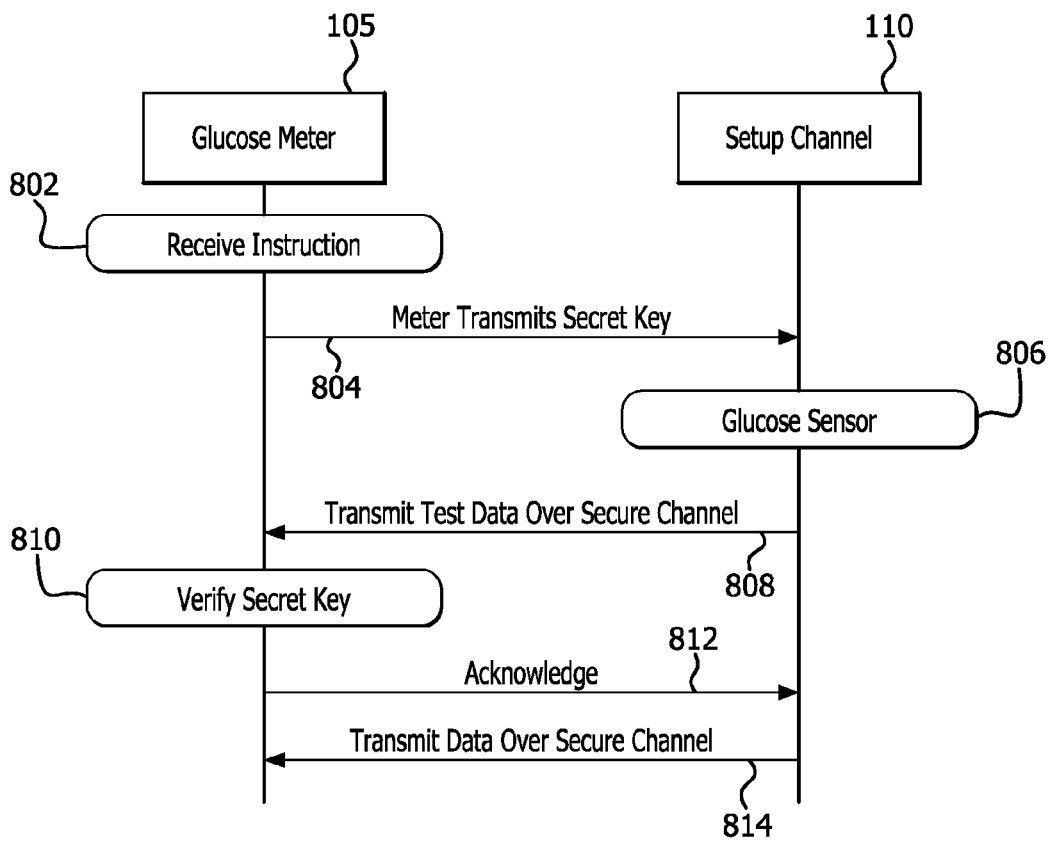

FIG. 8 illustrates another CGM system 100 that verifies successful reception of the secret key. At step 802, the glucose meter 105 receives an instruction to setup a secure wireless link with the glucose sensor 110. In response, the glucose meter 105 generates and transmits a secret key to the glucose sensor 110 at step 804. The glucose sensor 110 stores the secret key at step 806 to initiate setup the secure wireless link. Initially, the glucose sensor 110 transmits test data to the glucose meter 105 at step 808. The test data could be a random data or predetermined data that the glucose meter 105 also possesses. In the event the data is random, the transmitted data would include error check information to determine successful reception and decryption of the random data.

In response to receiving the test data, the glucose meter 105 decrypts the test data and determines if the test data was successfully received at step 810. If the test data is successfully received, the glucose meter 105 then determines that the secret key was successfully received by the glucose sensor 110. The glucose meter 105 then transmits an acknowledge message to the glucose sensor 110 via either the NFC link of the secure wireless channel at step 812. Upon reception of the acknowledge message, the glucose sensor 110 has fully setup the secure wireless channel and begins transmission of data using the secure wireless channel at step 814. In the event that the glucose meter 105 does not verify the secret key at 810, the sequence of communication would return to step 804 until the secret key is successfully determined to be received by the glucose sensor 110.

In accordance with an illustrative embodiment of the present invention, an inductive coupling link is provided to extend product shelf-life and improve patient data security of RF-controlled devices having factory-installed, non-accessible primary-cell batteries such as an internal sensor (such as an internal patch, subcutaneous sensor, or internal electrode, among other sensing devices). RF receiver circuitry for the heavily used bands available to such devices demodulates and examines received signals in order to determine whether the signal is of interest to the device. This can require too much power to be performed continuously. Therefore, low-power RF devices generally synchronize with their counterparts, and thereafter operate intermittently (e.g., on a predetermined schedule).

In the case of a sealed consumable product (such as an implanted consumable sensor 110), linked via RF communication to a reusable/durable user interface and control device (such as a durable handheld meter 105), deployment of a new device involves, in part, the synchronization and "pairing" of the consumable device and the durable device(s). In order for this initial, unscheduled exchange to take place, the consumable device must be listening for a message from an as-yet unknown instance of a durable device. Because the initial communication may occur days or months after manufacture, the consumable device's pre-synchronization listening would occur only at fairly infrequent intervals. The length of the interval would directly affect the user, as synchronization at time of deployment would require maintaining the new consumable device 30 within communication range of the durable device(s) for at least the length of this interval prior to use.

In accordance with an aspect of an illustrative embodiment of the present invention, the inductive coupling link augments the consumable device 110 by including a second means of communication between the durable device(s) 105 and the consumable device 110. This second communication mechanism is used, for example, in lieu of the normal RF link (that is, the RF link used during regular operation of the sensor 30 following initialization) for the purpose of initial synchronization and pairing. By employing inductive (quasi-static H-field) coupling with relatively simple modulation, for example, a passive detector on the consumable product 110 can draw its operating power from the signal itself, and remain ready-to-detect at all times without consuming battery power. This improves responsiveness of the sensor 110, while extending its shelf life.

The pairing operation mentioned above allows the durable device(s) 105 and consumable devices 110 to exchange cryptographic keys and identifying information that ensures that subsequent communication between the devices 110 and 105 is secure. The pairing operation itself, however, is vulnerable to attack. If the pairing is compromised, the security of subsequent operations may also be compromised. By using an inductive coupling link to perform certain steps of the pairing operation, however, the security of the transaction is greatly increased because of the unlikelihood of the short-range, relatively nonstandard inductive coupling transmission being correctly received and decoded.

It should further be appreciated that the nature of the inductive coupling described above is capable of delivering energy to the consumable device 110 from the durable device 105 via the inductive link, further lengthening the battery and shelf life of the consumable device 110.

A diabetes management system (e.g., a continuous glucose monitoring system) is described for illustrative purposes, but it is to be understood that the improved methods, devices and systems can be used for monitors or other devices for management of other physiological conditions such as, but not limited to, arrhythmia, heart failure, coronary heart disease, diabetes, sleep apnea, seizures, asthma, chronic obstructive pulmonary disease (COPD), pregnancy complications, tissue or wound state, state of wellness and fitness of a person (e.g., weight loss, obesity, heart rate, cardiac performance, dehydration rate, blood glucose, physical activity or caloric intake), or combinations thereof.

Some examples of a meter 105 can be, but is not limited to, a personal computer, a portable computer such as a laptop or a handheld device (e.g., personal digital assistant (PDA), iPod), mobile telephone such as a cellular telephone, Blackberry device, Palm device, or Apple iPhone device, a watch, a portable exercise device or other physiological data monitor (e.g., a meter connectable to a patient via a strap or incorporated into an article of clothing), among other user devices, each of which may be configured for data communication with the sensor or consumable device 110.

Some examples of measured or monitored physiological data include, but are not limited to ECG, EEG, EMG, SpO2, tissue impedance, heart rate, accelerometer, blood glucose, coagulation (e.g., PT-INR or prothrombin time (PT) and its derived measures of prothrombin ratio (PR) and international normalized ratio), respiration rate and airflow volume, body tissue state, bone state, pressure, physical movement, body fluid density, skin or body impedance, body temperature, patient physical location, or audible body sounds, among others, or a combination thereof.

The measured data can also be related to analytes such as, but not limited to, a substance or chemical constituent in a biological fluid (for example, blood, interstitial fluid, cerebral spinal fluid, lymph fluid or urine) that can be analyzed. Analytes can include naturally occurring substances, artificial substances, medicaments, metabolites, and/or reaction products. By way of examples, on or more analytes for measurement can be glucose; insulin; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-.beta. hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free .beta.-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, .beta.); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins and hormones naturally occurring in blood or interstitial fluids can also constitute analytes, for example. Further, the analyte can be naturally present in the biological fluid, for example, a metabolic product, a hormone, an antigen, an antibody, and the like. Alternatively, the analyte can be introduced into the body such as, for example but not limited to, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions can also be considered analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

Although only a few illustrative embodiments of the present invention have been described in detail above, those skilled in the art will readily appreciate that many modifications are possible in the illustrative embodiments without materially departing from the novel teachings and advantages of this invention. Accordingly, all such modifications are intended to be included within the scope of the appended claims and their equivalents.

What is claimed is:

1. A method for pairing a wireless physiological condition monitoring system, comprising:
    placing a physiological condition meter in proximity with a physiological condition sensor;
    receiving an instruction to initialize communication between the physiological condition meter and the physiological condition sensor;
    in response to the received instruction and the physiological condition meter being in proximity with the physiological condition sensor, generating a secret key at one of the physiological condition meter and the physiological condition sensor using a random process, and transmitting the secret key to the one of the physiological condition meter and the physiological condition sensor via a first communication link to provide a shared key that is shared between the physiological condition meter and the physiological condition sensor; and
    transmitting measurement data to the physiological condition meter from the physiological condition sensor via a secure wireless link based on the secret key;
    wherein the secret key is not generated until after the physiological condition meter and the physiological condition sensor are placed proximally to each other, and
    generating the secret key does not employ user input of an identifier of the physiological condition sensor.

2. The method of claim 1, further comprising encrypting the measurement data using the secret key.

3. The method of claim 2, wherein the first communication link is a near field communication (NFC) link formed when the physiological condition meter and the physiological condition sensor are proximate to each other.

4. The method of claim 3, wherein the secure wireless link is a radio frequency (RF) link.

5. The method recited in claim 3, further comprising:
    receiving operational information from the physiological condition sensor at the physiological condition meter via the first communication link, the operational information comprising at least one of battery status, expiration data, and spoilage of the physiological condition sensor; and
    determining if the physiological condition meter can transmit the secret key to the physiological condition sensor based on the operational information.

6. The method recited in claim 3, further comprising actuating the physiological condition sensor based on the received instruction.

7. The method recited in claim 6, wherein the received instruction comprises disposing the physiological condition sensor in a receptacle of the physiological condition meter, the receptacle configured to receive and actuate the physiological condition sensor.

8. The method of claim 3, wherein the physiological condition sensor comprises memory for storing the secret key that is programmable a single instance.

9. The method of claim 3, further comprising verifying if the physiological condition meter and the physiological condition sensor have identical secret keys.

10. The method of claim 3, wherein the NFC link is an inductive link and the range of the secure wireless link exceeds the range of the NFC link.

11. The method of claim 10, wherein the physiological condition meter and the physiological condition sensor are proximate when placed within approximately 20 centimeters.

12. The method of claim 3, further comprising the steps of:
    after placing the physiological condition meter in proximity with the physiological condition sensor, energizing an inductive element in the physiological condition meter, and inducing a current in an inductive element in the physiological condition sensor.

13. The method of claim 12, further comprising storing energy in the physiological condition sensor from the induced current.

14. The method of claim 12, further comprising the step of, when the inductive element in the physiological condition meter induces the current in the inductive element of the physiological condition sensor, sending the received instruction to initialize communication between the physiological condition meter and the physiological condition sensor.

15. The method of claim 2, wherein the first communication link is selected from at least one of an electrical connection, a wireless connection, an inductive coupling connection, and an optical connection.

16. A wireless physiological condition monitoring system, comprising:
    a physiological condition sensor for measuring physiological condition data of a user and transmitting the measured physiological condition data using a secure wireless link based on a secret key upon receiving an instruction to initialize communication between a physiological condition meter and the physiological condition sensor; and
    the physiological condition meter for receiving the measured physiological condition data via the secure wireless link based on the secret key and displaying the measured physiological condition data to the user,
    wherein, in response to the instruction provided when the physiological condition sensor and the physiological condition meter are in proximity to each other, the secret key is generated using a random process and transmitted using a second communication link;
    wherein the secret key is not generated until after the physiological condition meter and the physiological condition sensor are placed proximally to each other, and generating the secret key does not employ user input of an identifier of the physiological condition sensor.

17. The wireless physiological condition monitoring system of claim 16, wherein the physiological condition sensor encrypts the measured physiological condition data using the secret key and the physiological condition meter decrypts the encrypted measured physiological condition data using the secret key.

18. The wireless physiological condition monitoring system of claim 17, wherein the second communication link is a near field communication (NFC) link formed when the physiological condition meter and the physiological condition sensor are proximate to each other.

19. The wireless physiological condition monitoring system of claim 18 wherein the secure wireless link is a radio frequency (RF) link.

20. The wireless physiological condition monitoring system of claim 18, wherein the physiological condition meter receives operational information of the physiological condition sensor via the second communication link and determines if the physiological condition meter can transmit the secret key to the physiological condition sensor based on the operational information, the operational information comprising at least one of battery status, expiration data, and spoilage of the physiological condition sensor.

21. The wireless physiological condition monitoring system of claim 18, wherein the physiological condition sensor is actuated based on the instruction.

22. The wireless physiological condition monitoring system of claim 21, wherein the physiological condition meter includes a receptacle for receiving and actuating the physiological condition sensor.

23. The wireless physiological condition monitoring system of claim 18, wherein the physiological condition sensor includes a one time programmable memory for storing the secret key.

24. The wireless physiological condition monitoring system of claim 18, wherein the NFC link is an inductive link and the range of the secure wireless link exceeds the range of the NFC link.

25. The wireless physiological condition monitoring system of claim 24, wherein the physiological condition meter and the physiological condition sensor are proximate when placed within approximately 20 centimeters.

26. The wireless physiological condition monitoring system of claim 16, wherein the physiological condition sensor comprises a first inductive element adapted to provide an inductive link between the first inductive element and a second inductive element in the physiological condition meter.

27. The wireless physiological condition monitoring system of claim 26, wherein the instruction is generated and sent in response to an induced current of one of the first and second inductive elements induced by energization in the first and second inductive elements.

28. The wireless physiological condition monitoring system of claim 26, wherein the physiological condition sensor further comprises an energy storage element, and the energy storage element is adapted to be charged by an induced current in the first inductive element, the induced current being induced by energization of the second inductive element.

29. A method for synchronizing a wireless physiological condition monitoring system, comprising:
receiving an instruction to initialize communication between a physiological condition sensor and a physiological condition meter;
in response to the instruction, generating a secret key using a random process at one of the physiological condition meter and the physiological condition sensor and transmitting the secret key to the one of the physiological condition meter and the physiological condition sensor via a near field communication (NFC) wireless inductive link when the physiological condition meter is in proximity with the physiological condition sensor, the secret key not being generated until after the physiological condition meter and the physiological condition sensor are placed proximally to each other, and generating the secret key does not employ user input of an identifier of the physiological condition sensor;
receiving the secret key via the wireless inductive link;
encrypting data to be transmitted between the physiological condition sensor and physiological condition meter; and
transmitting the encrypted data between the physiological condition sensor and the physiological condition meter via a second wireless link.

30. The method of claim 29, wherein said receiving the instruction comprises at least one of receiving an indication that the physiological condition sensor is proximal to the physiological condition meter, receiving a user instruction, and receiving an indication that a detector has sensed the physiological condition sensor in a receptacle of the physiological condition meter.

31. The method of claim 29, further comprising:
receiving operational information from the physiological condition sensor at the physiological condition meter via the wireless inductive link; and
determining if the physiological condition meter can transmit the secret key to the physiological condition sensor based on the operational information;
wherein the operational information comprises at least one of battery status, expiration data, and spoilage of the physiological condition sensor.

* * * * *